(12) United States Patent
Huseman

(10) Patent No.: US 8,182,480 B2
(45) Date of Patent: May 22, 2012

(54) INSULATED TUBE FOR SUCTION COAGULATOR

(75) Inventor: Mark Huseman, Broomfield, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 889 days.

(21) Appl. No.: 12/194,254

(22) Filed: Aug. 19, 2008

(65) Prior Publication Data

US 2010/0049193 A1 Feb. 25, 2010

(51) Int. Cl.
*A61B 18/18* (2006.01)

(52) U.S. Cl. ............... 606/49; 606/41; 606/40; 606/32

(58) Field of Classification Search .................. 606/32, 606/47, 40–42, 49–52
See application file for complete search history.

(56) References Cited

U.S. PATENT DOCUMENTS

| | | | |
|---|---|---|---|
| 4,932,952 A | 6/1990 | Wojciechowicz, Jr. | |
| 5,133,714 A | 7/1992 | Beane | |
| 5,186,714 A | 2/1993 | Boudreault et al. | |
| 5,254,116 A * | 10/1993 | Baust et al. ................... 606/23 | |
| 5,277,696 A | 1/1994 | Hagen | |
| 5,290,282 A | 3/1994 | Casscells | |
| 5,334,140 A | 8/1994 | Phillips | |
| 5,380,277 A | 1/1995 | Phillips | |
| 5,451,223 A | 9/1995 | Ben-Simhon | |
| 5,520,685 A | 5/1996 | Wojciechowicz | |
| 5,683,366 A | 11/1997 | Eggers et al. | |
| 5,697,882 A | 12/1997 | Eggers et al. | |
| 5,700,262 A | 12/1997 | Acosta et al. | |
| 5,730,742 A * | 3/1998 | Wojciechowicz ............... 606/49 | |
| 5,925,045 A | 7/1999 | Reimels et al. | |
| 5,951,548 A | 9/1999 | DeSisto et al. | |
| 5,968,042 A | 10/1999 | Ernster | |
| 5,972,416 A | 10/1999 | Reimels et al. | |
| 5,989,249 A * | 11/1999 | Kirwan, Jr. ..................... 606/50 | |
| 6,027,501 A | 2/2000 | Goble et al. | |

(Continued)

FOREIGN PATENT DOCUMENTS

DE 2460481 12/1974

(Continued)

OTHER PUBLICATIONS

International Search Report from corresponding European Appl. No. EP 09 16 8059 mailed Jan. 26, 2010.

(Continued)

*Primary Examiner* — Jackie Ho
*Assistant Examiner* — Leah Stohr

(57) ABSTRACT

An electrosurgical suction coagulator includes a housing having proximal and distal ends and a substantially malleable elongated tube-like shaft extending longitudinally from a distal end thereof. The elongated tube-like shaft includes a tube-like outer wall having a tube-like dielectric sheath at least partially disposed thereon. A tube-like electrode is disposed coaxially through the tube-like outer wall and is configured to operably couple to a source of electrosurgical energy. A distal end of the tube-like electrode protrudes at least partially from a distal end of the tube-like outer wall and the tube-like electrode has at the distal end thereof at least one aspiration port defined therein. The tube-like electrode is adapted at the proximal end thereof to operably couple to a source of suction. A vacuum space is disposed concentrically between the tube-like electrode and the tube-like outer wall to impede the propagation of thermal energy along the tube-like shaft.

18 Claims, 2 Drawing Sheets

U.S. PATENT DOCUMENTS

| | | | |
|---|---|---|---|
| 6,032,673 | A | 3/2000 | Savage et al. |
| 6,063,079 | A | 5/2000 | Hovda et al. |
| 6,086,585 | A | 7/2000 | Hovda et al. |
| 6,149,620 | A | 11/2000 | Baker et al. |
| 6,156,036 | A * | 12/2000 | Sussman et al. ............... 606/48 |
| 6,190,381 | B1 | 2/2001 | Olsen et al. |
| 6,293,945 | B1 | 9/2001 | Parins et al. |
| 6,379,348 | B1 | 4/2002 | Onik |
| 6,379,350 | B1 | 4/2002 | Sharkey et al. |
| 6,406,476 | B1 | 6/2002 | Kirwan, Jr. et al. |
| 6,458,126 | B1 | 10/2002 | Doyle |
| 6,595,990 | B1 | 7/2003 | Weinstein et al. |
| 2002/0049438 | A1 | 4/2002 | Sharkey et al. |
| 2003/0181904 | A1 | 9/2003 | Levine et al. |
| 2004/0193150 | A1 | 9/2004 | Sharkey et al. |
| 2006/0235377 | A1 | 10/2006 | Earley et al. |
| 2008/0086120 | A1 | 4/2008 | Mirza et al. |

FOREIGN PATENT DOCUMENTS

| | | |
|---|---|---|
| DE | 2429021 | 1/1976 |
| DE | 3045996 | 7/1982 |
| DE | 3710489 | 11/1987 |
| DE | 4139029 | 6/1993 |
| DE | 4326037 | 2/1995 |
| DE | 9117019 | 4/1995 |
| DE | 19537897 | 3/1997 |
| DE | 9117299 | 4/2000 |
| DE | 19848784 | 5/2000 |
| DE | 29724247 | 8/2000 |
| EP | 0186369 | 7/1986 |
| EP | 0447121 | 9/1991 |
| EP | 0612535 | 8/1994 |
| EP | 0956827 | 11/1999 |
| EP | 1050279 | 8/2000 |
| EP | 1050277 | 11/2000 |
| EP | 1082945 | 3/2001 |
| EP | 1090597 | 4/2001 |
| EP | 1090599 | 4/2001 |
| EP | 1127551 | 8/2001 |
| EP | 1199037 A2 | 4/2002 |
| EP | 1199038 A2 | 4/2002 |
| EP | 1293171 | 3/2003 |
| EP | 1199037 A3 | 7/2003 |
| EP | 1199038 A3 | 7/2003 |
| EP | 1323384 A2 | 7/2003 |
| EP | 1323384 A3 | 1/2004 |
| EP | 1561430 | 8/2005 |
| EP | 1090598 | 9/2005 |
| EP | 1570798 | 9/2005 |
| EP | 1595507 | 11/2005 |
| EP | 1656900 | 5/2006 |
| EP | 1645234 | 12/2006 |
| EP | 1602337 | 12/2007 |
| FR | 1340509 | 9/1963 |
| FR | 2235669 | 1/1975 |
| GB | 014995 | 12/1965 |
| GB | 1014995 | 12/1965 |
| GB | 1222243 | 2/1998 |
| JP | 61-159953 | 7/1986 |
| SU | 1438745 | 11/1988 |
| WO | 91/13593 | 9/1991 |
| WO | 93/03678 | 3/1993 |
| WO | 94/20032 | 9/1994 |
| WO | 96/27337 | 9/1996 |
| WO | 96/39086 | 12/1996 |
| WO | 97/11647 | 4/1997 |
| WO | 98/43264 | 10/1998 |
| WO | 99/15091 | 4/1999 |
| WO | 01/62333 | 8/2001 |
| WO | 01/64122 | 9/2001 |
| WO | 02/47568 | 6/2002 |
| WO | 02/58762 | 8/2002 |
| WO | WO 03/061499 | 7/2003 |
| WO | 2004/010883 | 2/2004 |
| WO | 2004/045436 | 6/2004 |
| WO | 2004/073753 | 9/2004 |
| WO | 2005/016142 | 2/2005 |
| WO | 2005/060849 | 7/2005 |

OTHER PUBLICATIONS

Grund et al., "Endoscopic Argon Plasma . . . Flexible Endoscopy" Surgery and Allied Technologies, No. 1, vol. 2, pp. 42-46 (Feb. 1994).
Farin et al. "Technology of Argon Plasma . . . Endoscopic Applications" Endoscopic Surgery and Allied Technologies, No. 1, vol. 2, pp. 71-77 (Feb. 1994).
Brand et al. "Electrosurgical Debulking of Ovarian Cancer: A New Technique Using the Argon Beam Coagulator" Gynecologic Oncology 39.
Hernandez et al. "A Controlled Study of the Argon Beam Coagulator for Partial Nephrectomy" The Journal of Urology, vol. 143, May (J.Urol. 143: 1062-1065, 1990).
Ward et al. "A Significant New Contribution to Radical Head and Neck Surgery" Arch Otolaryngol Head Neck Surg., vol. 115, Aug. 1989 pp. 921-923.
Mark H. Mellow, "The Role of Endoscopic Laser Therapy in Gastrointestinal Neoplasms" Advanced Therapeutic Endoscopy, pp. 17-21.
Silverstein et al., "Thermal Coagulation Therapy for Upper Gastrointestinal Bleeding" Advanced Therapeutic Endoscopy, pp. 79-84.
Waye et al., "Techniques in Therapeutic Endoscopy", W.B.Saunders Company, Philadelphia, PA., pp. 1.7-1.15.
European Search Report for 01102843.8-2305 dated May 15, 2001.
International Search Report PCT/US98/19284, dated Jan. 14, 1999.
European Search Report for EP 05002257. 3 dated Jun. 1, 2005.
International Search Report for EP 06019572 dated Nov. 21, 2006.
European Search Report EP 07 00 4356 dated Jul. 2, 2007.
European Search Report EP 07 00 4659 dated Mar. 5, 2008.
European Search Report EP 00 12 1241 dated Jan. 17, 2001.
Valleylab in the OR; Tonsillectomy Article; Aug. 2005.
Valleylab Suction Coagulators; May 2009.
International Search Report from PCT-US03-37111 dated Jul. 21, 2004.
International Search Report from PCT-US04-04685 dated Aug. 6, 2004.
International Search Report from EP-0401-5980 dated Sep. 30, 2004.
International Search Report from PCT-US03-22900 dated Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.

* cited by examiner

INSULATED TUBE FOR SUCTION COAGULATOR

BACKGROUND

1. Technical Field

The present invention relates generally to electrosurgical coagulators and, more particularly, to an electrosurgical suction coagulator having improved thermal insulation between the active electrode and adjacent tissue.

2. Background of Related Art

The coagulation of bleeding blood vessels and tissue using electrically conductive suction tubes is a technique which has been widely used for some time. Typically, a combination electrosurgery and suction device is employed in surgery wherever excessive blood must be removed from the bleeding site in order to facilitate hemostasis of any bleeding vessels.

Electrosurgical suction coagulators which both coagulate and dissect tissue have also been available for some time. Generally, these devices include a shaft formed from a conductive suction tube electrode having an electrically insulating coating over all but a most distal portion of the tube, so that the distal portion forms a generally annular ablating electrode. The shaft may be formed of malleable materials to enable a surgeon to bend the shaft to a desired shape. The distal end can be used as a blunt dissection device and/or a blunt coagulator. A suction source is attached to a proximal portion of the tube for evacuating excess fluid and debris from the surgical site through the distal end of the tube. The electrode is operably coupled to a source of electrosurgical energy, such as an electrosurgical generator.

The described electrosurgical suction coagulators may have drawbacks. In particular, heat conducted from the suction tube electrode to the outer surface of the shaft may cause the surface of the shaft to reach temperatures of 60° C. or greater. This may be a concern during surgical procedures, such as an electrosurgical adenotonsillectomy, where the shaft of a suction coagulator may be in proximity to, or in contact with, anatomical structures unrelated to the procedure, such as the uvula or the oral commissure. The elevated shaft temperature may have undesirable effects on such unrelated anatomical structures, including uvular edema and erythema of the oral commissure area.

SUMMARY

According to an embodiment of the present disclosure, an electrosurgical suction coagulator includes a housing having proximal and distal ends and a substantially malleable elongated tube-like shaft extending longitudinally from the distal end thereof. The elongated tube-like shaft includes a tube-like outer wall having a tube-like dielectric sheath at least partially disposed thereon. A tube-like electrode is disposed coaxially through the tube-like outer wall and is configured to operably couple to a source of electrosurgical energy. The distal end of the tube-like electrode protrudes at least partially from the distal end of the tube-like outer wall and the tube-like electrode has at the distal end thereof at least one aspiration port defined therein. The tube-like electrode is adapted at the proximal end thereof to operably couple to a source of suction. A vacuum space is disposed concentrically between the tube-like electrode and the tube-like outer wall to impede the propagation of thermal energy from the tube-like shaft.

According to another embodiment of the present disclosure, an electrosurgical suction coagulator includes a housing having proximal and distal ends and a substantially malleable elongated tube-like shaft extending longitudinally from the distal end thereof. The elongated tube-like shaft includes a stainless steel tube-like outer wall having a tube-like dielectric sheath at least partially disposed thereon. A stainless steel tube-like electrode is disposed coaxially through the tube-like outer wall and is configured to operably couple to a source of electrosurgical energy. The distal end of the tube-like electrode protrudes at least partially from the distal end of the tube-like outer wall and the tube-like electrode has at the distal end thereof at least one aspiration port defined therein. The tube-like electrode is adapted at the proximal end thereof to operably couple to a source of suction. A thermal insulator is disposed at least partially on at least one of the tube-like outer wall and the dielectric sheath and a vacuum space is disposed concentrically between the tube-like electrode and the tube-like outer wall and is configured to impede the propagation of thermal energy from the tube-like shaft.

The present disclosure also provides a method of manufacturing an electrosurgical tool. The method includes coupling a proximal end of a substantially malleable elongate tube-like shaft to a distal end of a housing. The method also includes applying a tube-like dielectric sheath at least partially to a tube-like outer wall of the tube-like shaft. The method also includes coupling a tube-like electrode coaxially through the tube-like outer wall such that a distal end of the tube-like electrode protrudes at least partially from a distal end of the tube-like outer wall. The tube-like electrode has at the distal end thereof at least one aspiration port defined therein. The method also includes coupling a proximal end of the tube-like electrode to a source of suction via a lumen to provide fluid communication between the aspiration port and the source of suction. The method also includes electrically connecting the tube-like electrode to a source of energy to provide energy to tissue via the exposed distal end of the tube-like electrode. The method also includes evacuating a vacuum space disposed coaxially between the tube-like outer wall and the tube-like electrode to substantially impede the propagation of thermal energy from the tube-like shaft.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
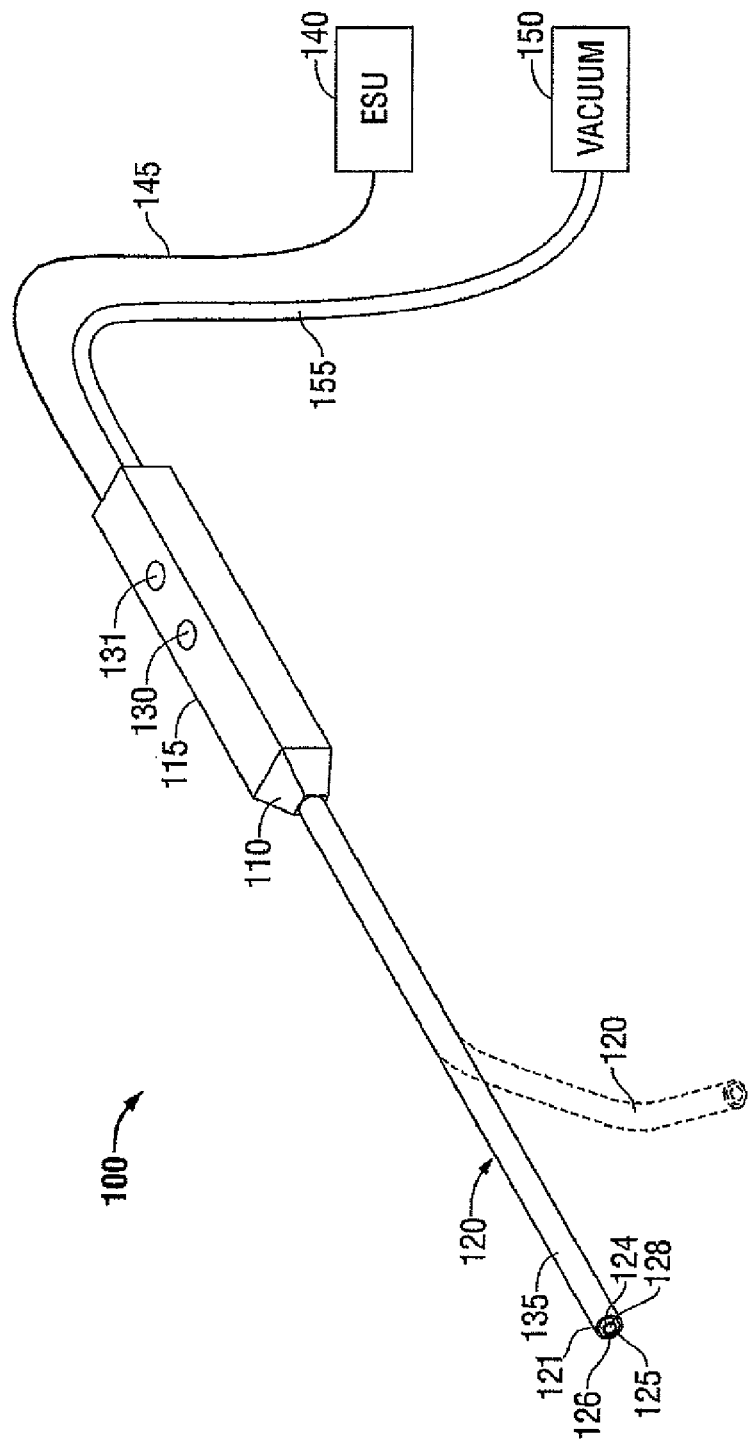
FIG. 1 is an oblique view of an exemplary embodiment of an electrosurgical suction coagulator system in accordance with the present disclosure.

Particular embodiments of the present disclosure are described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

With reference to FIG. 1, an electrosurgical suction coagulator system 100 is presented having a suction coagulator 110 that is operably coupled to an electrosurgical generator 140 via a conductor 145. Suction coagulator 110 is operably coupled to a vacuum source 150 by a lumen 155. Suction coagulator 110 includes a handle 115 disposed at the proximal end thereof and a elongated shaft 120 extending distally from the handle 115. Shaft 120 includes a tube-like outer wall 126 having an insulating sheath 135 at least partially disposed thereon. Insulating sheath 135 is formed from any suitable dielectric material, for example, polymeric materials such as PU, PVC, and the like. In use, insulating sheath 135 is configured to electrically insulate the outer surface of shaft 120 and/or tube-like outer wall 126 from the surgical site (e.g., the oral commissure and/or uvula of the patient). In embodiments, the tube-like outer wall 126 is formed from material having malleable or flexible properties, for example without limitation, metallic material such as stainless steel. The shaft 120 may be bent to a desired shape by the user, as shown by way of example by bent shaft 120' (shown in phantom).

In embodiments, shaft 120 includes a polyolefin heat shrink 121 applied at least partially thereto to provide thermal insulation to the outer surface of shaft 120. For example, the polyolefin heat shrink 121 may be applied between the tube-like outer wall 126 and the dielectric sheath 135. In this scenario, the polyolefin heat shrink 121 is applied to the outer surface of the tube-like outer wall 126 prior to the application of the dielectric sheath 135 to the tube-like outer wall 126. Additionally or alternatively, the polyolefin heat shrink 121 may be applied to the outer surface of the dielectric sheath 135. During use, the polyolefin heat shrink 121 operates to substantially impede the propagation of thermal energy from the tube-like shaft 120 to the surgical site.

Shaft 120 includes a tube-like electrode 125 configured to deliver electrosurgical energy to tissue. The electrode 125 is disposed coaxially through tube-like outer wall 126 and is exposed at a distal end 124 of shaft 120 to form an aspiration port 128 defined therethrough. Tube-like electrode 125 defines a conduit (not explicitly shown) longitudinally through shaft 120 for providing suction to a surgical site. By way of the conduit, the aspiration port 128 is in fluid communication with vacuum source 150 via lumen 155. The outer diameter of tube-like electrode 125 is sized smaller than the inner diameter of tube-like outer wall 126 to form a vacuum space (not explicitly shown) between tube-like electrode 125 and tube-like outer wall 126.

In an embodiment, handle 115 includes a control 130 (e.g., handswitch) configured to control the application of electrosurgical energy, i.e., activation and deactivation of an electrosurgical signal. Handle 115 includes an additional or second control 131 for controlling the application of suction to the surgical site. In embodiments, control 131 may be operably coupled to a valve (not shown) that may be disposed within handle 115, shaft 120, vacuum source 150, and/or lumen 155. In other embodiments, control 131 may be operably coupled to a regulator, motor control, or other suitable manner of vacuum control.

During use, the thermal conductance of the above-described system 100 operates to impede the propagation of thermal energy from the tube-like shaft 120 to the surgical site. Thermal conductance, as described herein, may refer to the thermal conductance of the system 100 or, alternatively, to the individual components of the system 100, for example, the vacuum space (described in more detail below with reference to FIG. 2A), the tube-like electrode 125, and the tube-like outer wall 126.

Figure 2A:
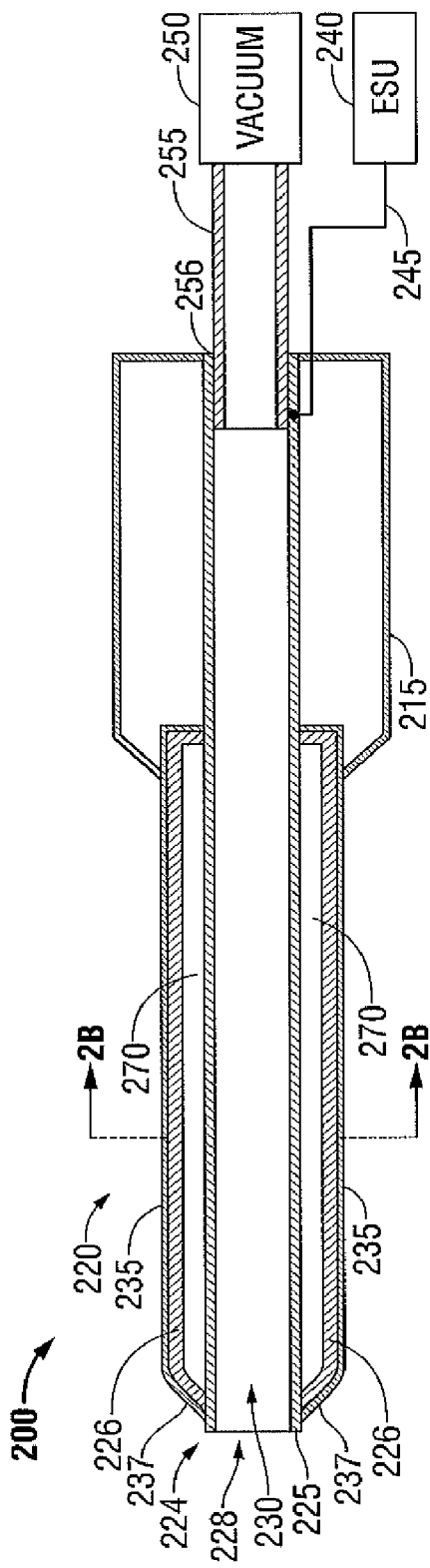
FIG. 2A is a side cutaway view of an embodiment of an electrosurgical suction coagulator in accordance with the present disclosure.
Figure 2B:
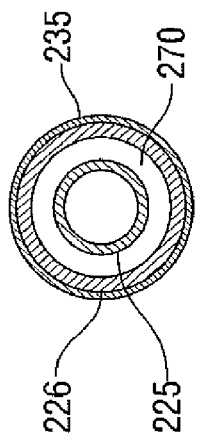
FIG. 2B is a section view of the electrosurgical suction coagulator of FIG. 2A.

Turning now to FIGS. 2A and 2B, a suction coagulator 200 in accordance with the present disclosure is operably coupled to an electrosurgical generator 240 via a conductor 245 and includes a housing 215 disposed proximally to an elongated shaft 220. Housing 215 may be a handle. Shaft 220 includes a tube-like outer wall 226 extending from housing 215 and having a substantially tapered distal end 237. Tube-like outer wall 226 includes an insulating sheath 235 at least partially disposed thereon configured to electrically insulate tube-like outer wall 226. Insulating sheath 235 is formed from any suitable dielectric material, for example, polymeric materials such as PU, PVC, and the like. In embodiments, the tube-like outer wall 226 is formed from material having malleable or flexible properties, for example without limitation, metallic material such as stainless steel.

A tube-like electrode 225 configured to deliver electrosurgical energy to tissue is disposed coaxially though shaft 220 and is exposed at a distal end 224 of shaft 220 to form an aspiration port 228 defined therethrough. Tube-like electrode 225 defines a conduit 230 longitudinally through shaft 220 for providing suction to a surgical site. Conduit 230 is in fluid communication with vacuum source 250 via lumen 255. By way of the conduit 230, the aspiration port 228 is in fluid communication with vacuum source 250 via lumen 255. The outer diameter of tube-like electrode 225 is sized smaller than the inner diameter of tube-like outer wall 226 such that tube-like electrode 225 is disposed concentrically within tube-like outer wall 226 to form a vacuum space 270 therebetween. The vacuum space 270 may include a suitable valve mechanism or conduit (not explicitly shown) configured to connect to a vacuum pump (not explicitly shown). Once suction coagulator 200 is assembled, the vacuum pump is used to evacuate the vacuum space 270. In use, vacuum space 270 is configured to substantially impede the propagation of thermal energy between tube-like electrode 225 and tube-like outer wall 226.

In embodiments, tube-like electrode 224 is formed from stainless steel. The substantially tapered distal end 237 of tube-like outer wall 226 is coupled and/or sealed to tube-like electrode 225 at a distal end 224 of shaft 220 by any suitable coupling technique or combination of coupling techniques such as, for example, crimping, welding, soldering, adhesive, etc.

In embodiments, shaft 220 includes a polyolefin heat shrink (not explicitly shown) applied at least partially thereto to provide thermal insulation to the outer surface of shaft 220. For example, a polyolefin heat shrink may be applied between the tube-like outer wall 226 and the dielectric sheath 235. In this scenario, the polyolefin heat shrink is applied to the outer surface of the tube-like outer wall 226 prior to the application of the dielectric sheath 235 to the tube-like outer wall 226. Additionally or alternatively, the polyolefin heat shrink may be applied to the outer surface of the dielectric sheath 235. During use, the polyolefin heat shrink operates to substantially impede the propagation of thermal energy from the tube-like shaft 220 to the surgical site.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An electrosurgical suction coagulator, comprising:
   a housing having proximal and distal ends and a substantially malleable elongated tube-like shaft extending longitudinally from a distal end thereof, the elongated tube-like shaft defining a cavity and including:
   a tube-like outer wall having a tube-like dielectric sheath at least partially disposed thereon;
   a tube-like electrode disposed coaxially through said cavity and configured to operably couple to a source of electrosurgical energy, wherein a distal end of the tube-like electrode protrudes at least partially from a distal end of the tube-like outer wall, the tube-like electrode having at the distal end thereof at least one aspiration port defined therein, the tube-like electrode being adapted at the proximal end thereof to operably couple to a source of suction; and
   a sealable vacuum space disposed concentrically between the tube-like electrode and the tube-like outer wall to impede the propagation of thermal energy along the tube-like shaft.

2. An electrosurgical suction coagulator according to claim 1, wherein at least one of the tube-like outer wall and the tube-like electrode are made from stainless steel.

3. An electrosurgical suction coagulator according to claim 1, wherein the tube-like shaft includes a thermal insulator disposed at least partially on at least one of the tube-like outer wall and the dielectric sheath.

4. An electrosurgical suction coagulator according to claim 3, wherein the thermal insulator is a polyolefin heat shrink.

5. An electrosurgical suction coagulator according to claim 1, wherein the tube-like outer wall has a substantially tapered distal end configured to be coupled to the tube-like electrode at a distal end of the tube-like shaft.

6. An electrosurgical suction coagulator according to claim 5, wherein the substantially tapered distal end of the tube-like outer wall is coupled to the tube-like electrode via at least one of welding, crimping, soldering, and adhesive.

7. An electrosurgical suction coagulator according to claim 1, wherein the tube-like outer wall is made from the same material as the tube-like electrode.

8. An electrosurgical suction coagulator according to claim 1, wherein the tube-like outer wall and the tube-like electrode are made from the same materials, the materials having a thermal conductance substantially equivalent to each other.

9. An electrosurgical suction coagulator according to claim 1, further comprising at least one control that activates at least one of the source of electrosurgical energy and the source of aspiration suction.

10. An electrosurgical suction coagulator according to claim 1, wherein the tube-like electrode defines a conduit adapted to couple to the source of suction to provide fluid communication between the at least one aspiration port and the source of suction.

11. An electrosurgical suction coagulator according to claim 1, wherein the tube-like shaft is selectively deformable.

12. An electrosurgical suction coagulator, comprising:
    a housing having proximal and distal ends and a substantially malleable elongated tube-like shaft extending longitudinally from a distal end thereof, the elongated tube-like shaft defining a cavity and including:
    a stainless steel tube-like outer wall having a tube-like dielectric sheath at least partially disposed thereon;
    a stainless steel tube-like electrode disposed coaxially through said cavity and configured to operably couple to a source of electrosurgical energy, wherein a distal end of the tube-like electrode protrudes at least partially from a distal end of the tube-like outer wall, the tube-like electrode having at the distal end thereof at least one aspiration port defined therein, the tube-like electrode being adapted at a proximal end thereof to operably couple to a source of suction;
    a thermal insulator disposed at least partially on at least one of the tube-like outer wall and the dielectric sheath; and
    a sealable vacuum space disposed concentrically between the tube-like electrode and the tube-like outer wall and configured to impede the propagation of thermal energy along the tube-like shaft.

13. An electrosurgical suction coagulator according to claim 12, wherein the thermal insulator is a polyolefin heat shrink.

14. A method of manufacturing an electrosurgical tool, comprising the steps of:
    coupling a proximal end of a substantially malleable elongate tube-like shaft defining a cavity to a distal end of a housing;
    applying a tube-like dielectric sheath at least partially to a tube-like outer wall of the tube-like shaft;
    coupling a tube-like electrode coaxially through said cavity such that a distal end of the tube-like electrode protrudes at least partially from a distal end of the tube-like outer wall, the tube-like electrode having at the distal end thereof at least one aspiration port defined therein;
    coupling a proximal end of the tube-like electrode to a source of suction via a lumen defined therein to provide fluid communication between the aspiration port and the source of suction;
    electrically connecting the tube-like electrode to a source of energy to provide energy to tissue via the exposed distal end of the tube-like electrode; and
    evacuating a sealable vacuum space disposed coaxially between the tube-like outer wall and the tube-like electrode to substantially impede the propagation of thermal energy along the tube-like shaft.

15. A method of manufacturing an electrosurgical tool according to claim 14, further comprising the step of:
    applying a thermal insulator at least partially to at least one of the tube-like outer wall and the tube-like dielectric sheath.

16. A method of manufacturing an electrosurgical tool according to claim 14, wherein at least one of the tube-like outer wall and the tube-like electrode is made from stainless steel.

17. A method of manufacturing an electrosurgical tool according to claim 14, further comprising the step of:
    coupling the substantially tapered end of the tube-like outer wall to the tube-like electrode via at least one of welding, crimping, soldering, and adhesive.

18. A method of manufacturing an electrosurgical tool according to claim 14, wherein the tube-like outer wall has a thermal conductance substantially equivalent to the thermal conductance of the tube-like electrode.

* * * * *